(12) United States Patent
Segermark

(10) Patent No.: US 9,039,713 B2
(45) Date of Patent: May 26, 2015

(54) RELEASABLY ATTACHED SNARE LOOP RETRIEVAL DEVICE AND METHOD OF USING THE SAME

(75) Inventor: James D. Segermark, Gem Lake, MN (US)

(73) Assignee: Merit Medical Systems, Inc., South Jordan, UT (US)

( * ) Notice: Subject to any disclaimer, the term of this patent is extended or adjusted under 35 U.S.C. 154(b) by 268 days.

(21) Appl. No.: 13/106,995

(22) Filed: May 13, 2011

(65) Prior Publication Data

US 2012/0289945 A1    Nov. 15, 2012

(51) Int. Cl.
- A61B 17/00    (2006.01)
- A61B 17/221    (2006.01)
- A61B 17/34    (2006.01)
- A61B 17/22    (2006.01)

(52) U.S. Cl.
CPC . A61B 17/00234 (2013.01); A61B 2017/00358 (2013.01); A61B 2017/3445 (2013.01); A61B 17/221 (2013.01); A61B 2017/00473 (2013.01); A61B 2017/22039 (2013.01)

(58) Field of Classification Search
CPC .............. A61B 2018/141; A61B 2018/1407; A61B 2017/3445; A61B 2017/2212; A61B 2017/22039; A61B 2017/00473; A61B 2017/0046; A61B 2017/00358; A61B 17/32056; A61B 17/221; A61B 17/00234; A61B 1/00101
USPC ............................................ 606/113, 114, 79
See application file for complete search history.

(56) References Cited

U.S. PATENT DOCUMENTS

| | | | |
|---|---|---|---|
| 5,171,233 A | 12/1992 | Amplatz et al. | |
| 5,290,294 A | 3/1994 | Cox et al. | |
| 5,352,219 A * | 10/1994 | Reddy | 606/1 |
| 5,417,684 A * | 5/1995 | Jackson et al. | 606/1 |
| 5,460,610 A | 10/1995 | Michael | |
| 5,562,678 A | 10/1996 | Booker | |
| 5,613,973 A | 3/1997 | Jackson et al. | |
| 5,782,839 A | 7/1998 | Hart et al. | |
| 5,860,987 A | 1/1999 | Ratcliff et al. | |
| 5,911,725 A | 6/1999 | Boury | |
| 5,961,526 A | 10/1999 | Chu et al. | |
| 5,971,994 A | 10/1999 | Fritzsch | |
| 6,059,796 A | 5/2000 | Bilitz et al. | |
| 6,071,233 A | 6/2000 | Ishikawa et al. | |

(Continued)

FOREIGN PATENT DOCUMENTS

| | | |
|---|---|---|
| EP | 0169784 | 7/1985 |
| EP | 1757234 | 7/2006 |

(Continued)

OTHER PUBLICATIONS

U.S. Appl. No. 13/014,427, Publication Date Jan. 26, 2011, Hewitt et al.

(Continued)

*Primary Examiner* — Thomas McEvoy
*Assistant Examiner* — Julie A Szpira
(74) *Attorney, Agent, or Firm* — Stoel Rives LLP

(57) ABSTRACT

A retrieval device with releasably attached loops is disclosed. Attachment portions on one or both ends of the shaft of the snare device may allow one or more loops to be coupled or de-coupled from the shaft. The retrieval device may further comprise a delivery conduit configured to receive both a snare shaft and a guidewire in one or more lumens.

15 Claims, 4 Drawing Sheets

(56) References Cited

U.S. PATENT DOCUMENTS

| | | | |
|---|---|---|---|
| 6,093,195 | A | 7/2000 | Ouchi |
| 6,174,318 | B1 | 1/2001 | Bates et al. |
| 6,193,672 | B1 | 2/2001 | Clement |
| 6,458,145 | B1 | 10/2002 | Ravenscroft et al. |
| 6,517,550 | B1 | 2/2003 | Konya et al. |
| 2002/0123698 | A1 | 9/2002 | Garibotto et al. |
| 2002/0123765 | A1 | 9/2002 | Sepetka et al. |
| 2002/0183781 | A1 | 12/2002 | Casey et al. |
| 2002/0188262 | A1 | 12/2002 | Abe |
| 2003/0021446 | A1 | 1/2003 | Dietz et al. |
| 2004/0059345 | A1 | 3/2004 | Nakao et al. |
| 2004/0068226 | A1 | 4/2004 | Brannon |
| 2004/0153095 | A1 | 8/2004 | Seddon |
| 2005/0171566 | A1 | 8/2005 | Kanamaru |
| 2005/0209609 | A1 | 9/2005 | Wallace |
| 2005/0234474 | A1 | 10/2005 | De Mello et al. |
| 2006/0090761 | A1 | 5/2006 | Kurrus |
| 2006/0116702 | A1 | 6/2006 | Goto et al. |
| 2007/0129719 | A1* | 6/2007 | Kendale et al. ............ 606/41 |
| 2007/0162047 | A1 | 7/2007 | Gasche |
| 2007/0162048 | A1 | 7/2007 | Quinn et al. |
| 2007/0191866 | A1 | 8/2007 | Palmer et al. |
| 2007/0260264 | A1 | 11/2007 | Nobis et al. |
| 2008/0086149 | A1 | 4/2008 | Diamant et al. |
| 2008/0188866 | A1 | 8/2008 | Karpiel et al. |
| 2009/0030427 | A1* | 1/2009 | Razvi et al. ............ 606/127 |
| 2009/0069806 | A1 | 3/2009 | De La Mora Levy et al. |
| 2009/0112244 | A1 | 4/2009 | Freudenthal |
| 2009/0118760 | A1 | 5/2009 | Clausen et al. |
| 2009/0131749 | A1 | 5/2009 | Ahmed et al. |
| 2010/0087781 | A1 | 4/2010 | Adams et al. |

FOREIGN PATENT DOCUMENTS

| | | |
|---|---|---|
| JP | 2005270464 | 10/2005 |
| WO | WO02/43600 | 6/2002 |
| WO | WO 2008/045143 | 4/2008 |
| WO | WO 2010/002549 | 1/2010 |

OTHER PUBLICATIONS

U.S. Appl. No. 13/105,653, Publication Date May 11, 2011, Segermark et al.
International Search Report and Written Opinion dated Mar. 18, 2011 for PCT/US2011/022509.
U.S. Appl. No. 13/343,570, Publication Date Jan. 4, 2012, Lampropoulos et al.
U.S. Appl. No. 13/343,550, Publication Date Jan. 4, 2002, Lampropoulos et al.
International Search Report and Written Opinion dated May 1, 2012 for PCT/US2012/020204.
International Search Report and Written Opinion dated May 3, 2012 for PCT/US2012/020208.
International Search Report and Written Opinion dated Aug. 13, 2012 for PCT/US12/36144.
International Search Report and Written Opinion dated Aug. 16, 2012 for PCT/US12/36125.
Office Action dated Aug. 17, 2012 for U.S. Appl. No. 13/014,427.
Office Action dated Sep. 26, 2012 for U.S. Appl. No. 13/106,995.
Office Action dated Mar. 13, 2013 for U.S. Appl. No. 13/105,653.
Office Action dated Mar. 28, 2013 for U.S. Appl. No. 13/343,570.
Office Action dated Apr. 15, 2013 for U.S. Appl. No. 13/014,427.
Office Action dated Jul. 19, 2013 for U.S. Appl. No. 13/343,570.
Notice of Allowance dated Oct. 9, 2013 for U.S. Appl. No. 13/014,427.
Extended European Search Report dated Mar. 31, 2014 for EP 12732457.2.
Office Action dated Apr. 29, 2014 for U.S. Appl. No. 13/343,550.
Office Action dated Jun. 10, 2014 for U.S. Appl. No. 13/343,570.
Extended European Search Report dated Aug. 6, 2014 for EP 12732501.7.

* cited by examiner

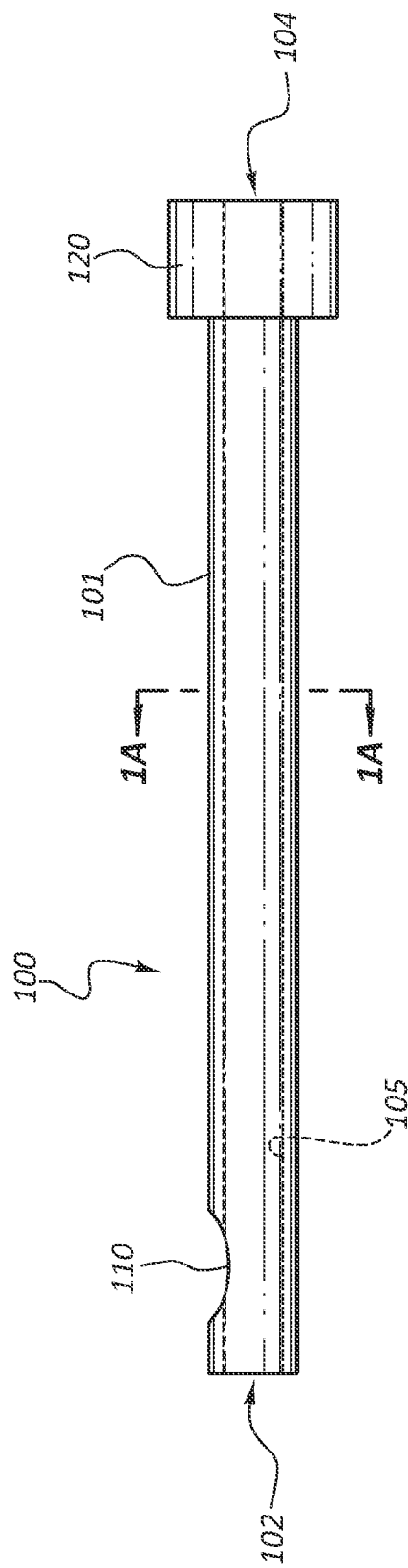
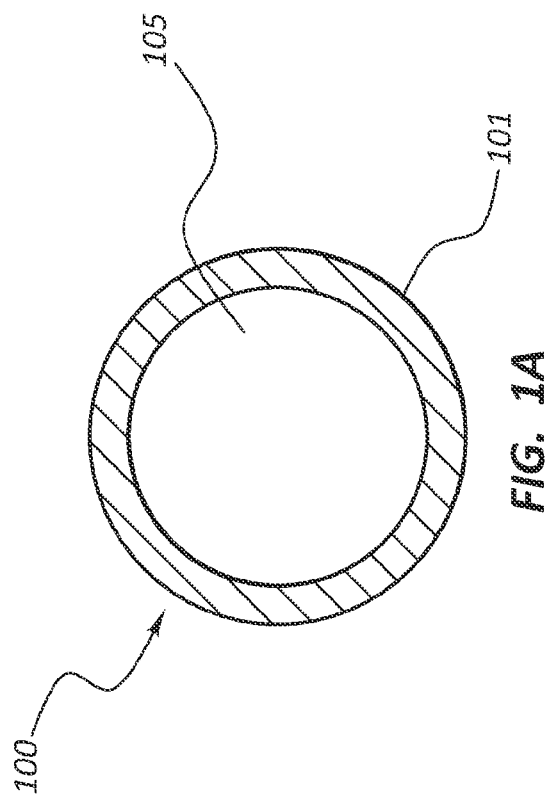

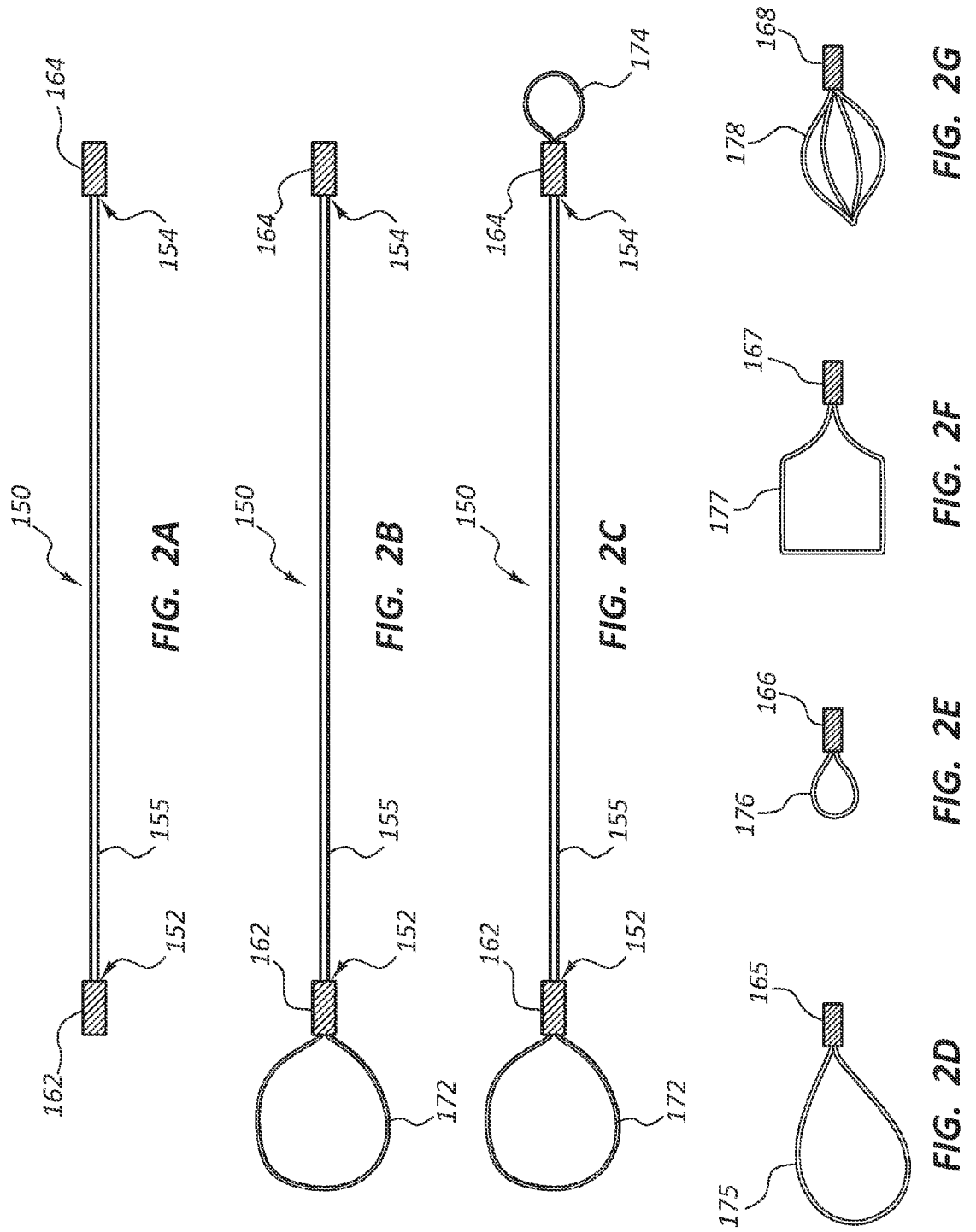

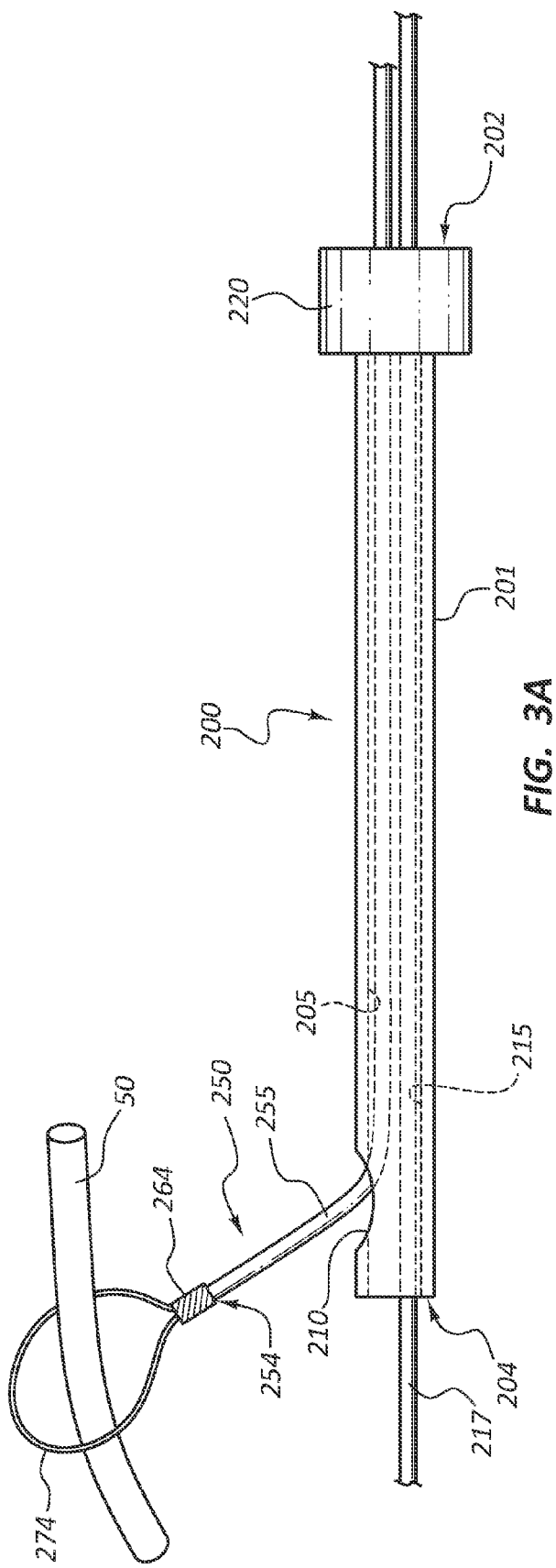
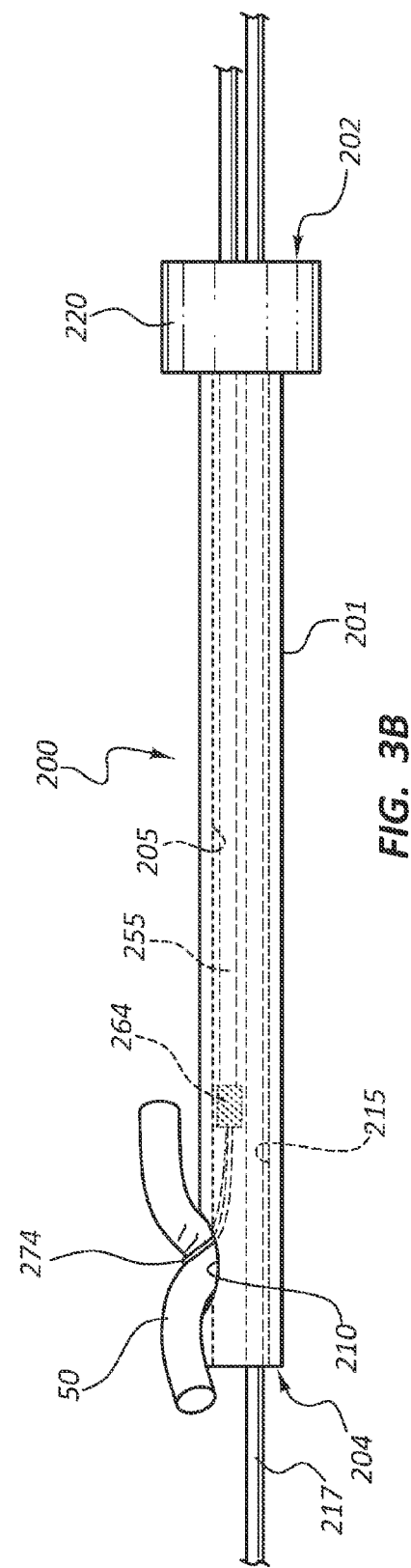
FIG. 3A
FIG. 3B

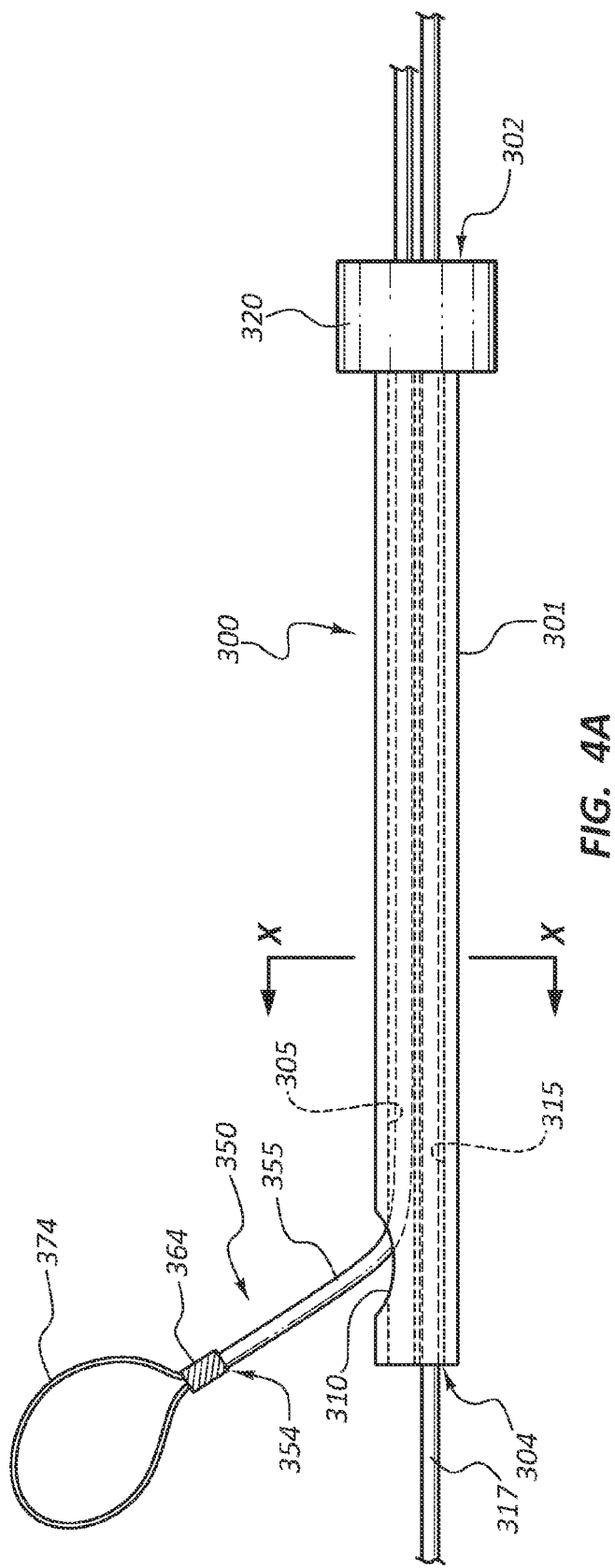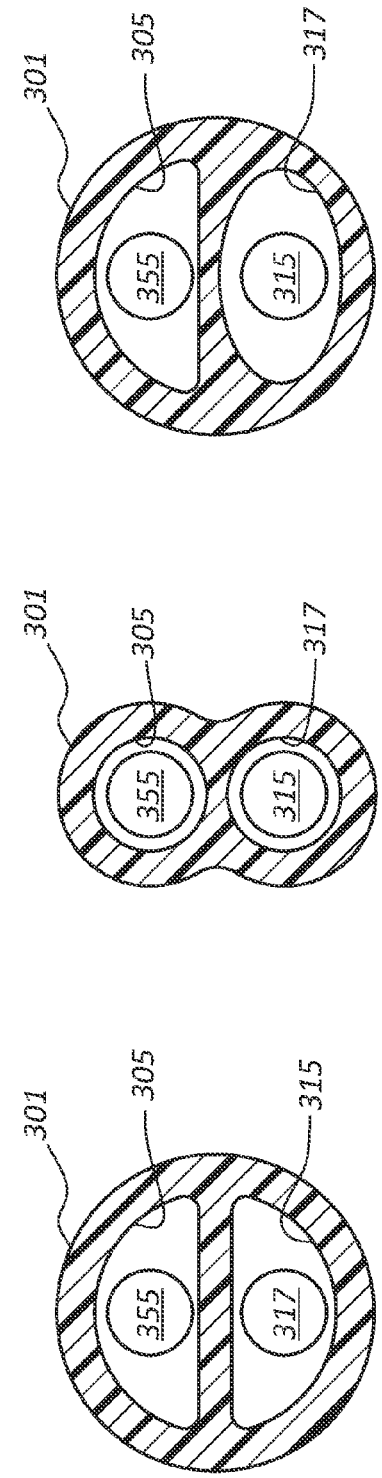

RELEASABLY ATTACHED SNARE LOOP RETRIEVAL DEVICE AND METHOD OF USING THE SAME

TECHNICAL FIELD

The present disclosure relates generally to devices used to retrieve or manipulate items or structures located in anatomically remote locations, such as items located in body lumens. More specifically, the present disclosure relates to retrieval devices, such as snares, which may be configured with releasably coupled snare loops.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1 is a side view of a delivery conduit.

FIG. 1A is a cross sectional view through lines 1A-1A of the delivery conduit of FIG. 1.

FIG. 2A is a side view of a shaft of a snare device with two attachment portions.

FIG. 2B is a side view of the shaft of FIG. 2A with one snare loop coupled to the shaft.

FIG. 2C is a side view of the shaft of FIGS. 2A and 2B with two snare loops coupled to the shaft.

FIGS. 2D, 2E, 2F, and 2G are alternate embodiments of snare loops.

FIG. 3A is a side view of a snare device in use.

FIG. 3B is a side view of the snare device of FIG. 3A in a second position.

FIG. 4A is a side view of a snare device.

FIGS. 4B, 4C, and 4D are possible cross sectional views of the snare device of FIG. 4A taken through lines X-X.

DETAILED DESCRIPTION

A snare device may be configured with one or more releasably coupled snare loops. Such a device may provide versatility, allowing a practitioner to select a particular snare loop based upon characteristics of the loop (such as size or shape) and the parameters of the therapy.

It will be readily understood that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use.

"Delivery conduit," as used herein, refers to an artificial channel capable of establishing communication between a remote location and an external environment. For example, in certain embodiments described herein, the delivery conduit comprises the outer sheath of a snare device, which in some embodiments comprises a catheter.

As used herein, "fragment" means either a foreign object disposed within a body lumen or an anatomical structure within the body which requires ligation or removal.

Further, as used herein, a "snare device" refers to a medical device with an elongate shape having at least one "snare loop." Thus, a snare device may or may not include a delivery conduit or outer sheath member. As used herein, a "snare loop" refers to a closed shape configuration of an elongate member, such as a wire. The term is not limited to "loops" with generally circular shapes, but includes any variety of shapes, including, for example, square loops, rectangular loops, ellipsoidal loops, trapezoidal loops, etc. Furthermore, a snare "loop" may also include "basket" type loops which are formed of multiple strands of wire or other material to form a basket-like enclosure rather than a single flat enclosed shape.

FIG. 1 is a side view of a delivery conduit 100, or catheter, having a single lumen 105. In the illustrated embodiment, the lumen 105 extends the length of the delivery conduit 100 from the proximal end 104 of the delivery conduit 100 to the distal end 102 of the delivery conduit 100. As also shown in FIG. 1A, the delivery conduit 100 and the lumen 105 may define a side wall 101 of the delivery conduit. The side wall 101 may be defined as the portion of the delivery conduit 100 surrounding the lumen where the outer surface of the side wall runs generally parallel to the longitudinal axis of the delivery conduit 100. In some embodiments, the delivery conduit may have a distal opening 110 which allows the lumen 105 to be in communication with the environment outside the distal end 102 of the delivery conduit 100. The distal opening 110 may be an opening in the side wall 101 of the delivery conduit 100. In the illustrated embodiment, distal opening 110 extends through the side wall 101 of the delivery conduit 100, allowing access from the lumen 105 to an area outside the delivery conduit 100. In embodiments where the distal opening 110 is in a side wall 101 of the delivery conduit 100, the distal opening 110 may constitute a removed area of from about 5% to about 48% of the circumference of the side wall 101 of the delivery conduit. In other embodiments, the distal opening 110 may fall into a smaller range of values, for example from about 25% to about 48% of the circumference of the delivery conduit. In still other embodiments, the distal opening 110 may be in a different location on the delivery conduit 100, such as in the distal end 102 of the delivery conduit 100.

In certain embodiments, the delivery conduit 100 may also be configured with a connector 120 to couple the delivery conduit 100 to another device. This connector 120 may be any type of connector known in the art, for example, a luer connector.

The delivery conduit 100 may define an outer sheath through which medical devices (for example, guidewires or snare devices) may pass during therapy. It will be appreciated that medical devices disposed within the delivery conduit 100 may be configured to be longitudinally displaceable with respect to the delivery conduit 100 during use.

The delivery conduit 100 may be made from any extrudable, medical grade plastic such as those commonly used for making catheters. Examples include but are not limited to polyurethane, polyethylene (varying densities), PET (polyethylene terephthalate), PVC, polypropylene, nylon, pebabyx, ABS, Hytrel®, Santoprene®, polycarbonate, Kraton®, PES, PVDF, and FEP.

FIG. 2A is a side view of an elongate shaft 155 of a snare device 150. The elongate shaft 155 may have a first end 152 and a second end 154. The shaft may be comprised of a single, wire like member, multiple small wire members twisted or braided together, or any other configuration as known in the art. The shaft 155 may have an attachment portion 162, 164 at one or both ends 152, 154 of the shaft 155. In the illustrated embodiment, the shaft 155 has a first attachment portion 162 at the first end 152 of the shaft 155 and a second attachment portion 164 at the second end 154 of the shaft 155.

FIG. 2B is a side view of the elongate shaft 155 of FIG. 2A with a first snare loop 172 coupled to the shaft 155 at the first end 152 of the shaft 155. In the illustrated embodiment, the first loop 172 is coupled to the first end 152 of the shaft 155 through use of the first attachment portion 162.

FIG. 2C is a side view of the elongate shaft 155 of FIGS. 2A and 2B with a first loop 172 coupled to the first end 152 as in FIG. 2B, and a second loop 174 coupled to the second end 154 of the elongate shaft 155. The second loop 174 is coupled to the second end 154 of the shaft 155 through use of the second attachment portion 164.

The embodiment illustrated in FIGS. 2A-2C includes attachment portions 162, 164 at both ends 152, 154 of the elongate shaft 155. In other embodiments, the shaft 155 may only have a single attachment portion on a single end of the shaft 155.

FIGS. 2D, 2E, 2F, and 2G illustrate alternate embodiments of possible snare loops 175, 176, 177, 178 that may be configured with attachment portions 165, 166, 167, 168 for use with an elongate shaft such as shaft 155 in FIGS. 2A, 2B, and 2C. It will be appreciated that the loops 175, 176, 177, 178 are illustrative and other configurations of loops (such as variations in size, shape, number of loops used together and material) may be used within the scope of this disclosure. A possible difference between exemplary snare loops includes loops which are of different sizes; that is, that a first loop circumscribes a greater area, by comparison, than a second loop. Additionally, loops may be of differing shapes, for example, the loop illustrated in FIG. 2F is substantially square in shape while the loops of FIGS. 2D and 2E are generally rounded. Moreover, a loop may consist of multiple strands which form a "basket" type loop, such as that illustrated in FIG. 2G. While the embodiment of FIG. 2G is a basket formed of four strands, it will be understood that other embodiments could be formed using more or fewer strands.

Loops, such as those illustrated in FIGS. 2D, 2E, 2F, and 2G, may be coupled to a shaft, such as that illustrated in FIGS. 2A, 2B, and 2C, through use of an attachment portion. While "attachment portions" are illustrated on each of FIGS. 2A-2G (in some instances on the loops and on some instances on the shaft) it will be appreciated that the attachment portions illustrated, 162, 164, 165, 166, 167, 168 are meant as representations of any device or structure which may be used to couple a loop to a shaft. Thus, the illustrated "attachment portions" are representative in nature, the illustration is does not necessarily resemble any particular structure for coupling the two components. Further, it will be appreciated that, in some instances, the "attachment portion" may consist of a structure or component initially fixed to the shaft and not to the loop, to the loop and not to the shaft, or one or more mating components may be attached to both the loop and to the shaft.

One example of a coupling component that may be initially fixed to only the loop is a flute and collet assembly. As known in the art, a collet may be use in connection with flutes to grip or clamp an elongate member or part. Thus, a loop may be configured with a flute and collet assembly fixed to a portion of the loop. The snare loop may then be coupled to a shaft simply by using the flute and collet assembly to clamp or grip one end of the shaft. Thus, in this example, the structure of the "attachment portion" is fixed to the loop prior to coupling the loop to the shaft. Alternatively, the flute and collet assembly could be fixed to the shaft and used to grip an elongate portion of the loop.

In other embodiments, the attachment portion may have components that are initially fixed to both the loop and the shaft. For example, the shaft may be fixed to a component which includes threads and the loop fixed to a component with mating threads. The shaft and the loop could thus be coupled by engaging the two threaded components. It will be appreciated that either the loop or the shaft could be fixed to a component with either external or internal threads.

Any attachment mechanism or component known in the art may be used to attach a loop to a shaft, as described herein. For example, clamps, chucks, collets, flutes, threads, interference fits (including tapered components and components with mating shoulders and flanges), pins, clips, retaining rings, or barbed connectors may all be used to couple a loop to a shaft. It will be appreciated that a variety of connectors used in other mechanical arts can also be adapted for use with a snare loop and shaft, for example, connectors used in connecting pneumatic hoses, hydraulic lines, or electrical wires may be so adapted. In some embodiments, the attachment portion will be configured such that a loop may be coupled and/or decoupled by a medical practitioner directly. In some instances this will include situations where the practitioner may couple or decouple a loop as part of the therapeutic procedure. In differing embodiments, tools may or may not be required to couple and/or decouple a loop from a shaft.

In some embodiments, the attachment portion may be configured such that, once a loop is coupled to a snare shaft, it cannot be decoupled. In other embodiments, the attachment portion may be configured such that a first loop may be coupled to the shaft, decoupled, and a second loop coupled to the shaft in the place of the first loop. As used herein, "releasably couplable" refers to a configuration where a loop is configured to be decoupleable from a shaft after it has been coupled, including embodiments where a practitioner may decouple the loop from the shaft. Further, in certain embodiments, any number of loops could be coupled and decoupled to the same attachment portion of a shaft. In still other embodiments, the attachment portion may be configured such that, while a loop may be coupled or decoupled from the shaft, the loop may not be decoupled remotely. For instance, decoupling may require direct input from a practitioner and configured such that the loop will not readily become accidentally decoupled during use.

In some instances, the attachment member can be utilized to provide versatility and adaptability during therapy. The attachment member may be configured such that a practitioner may directly couple and decouple loops from a snare device shaft. Thus, a practitioner may be able to select one or more particular loops for use in a particular therapy, thus "customizing" the snare device for the particular therapy and patient.

For example, a practitioner may begin a therapeutic procedure by first positioning a delivery conduit within the body of a patient. The practitioner may then determine an appropriate snare loop for the necessary therapy (based on the size or shape of the loop, the material from which the loop is formed, and so on). The practitioner may then couple the selected loop to an end of a shaft which initially has no loops (such as the shaft illustrated in FIG. 2A). After coupling this first loop to a first end of the shaft, the practitioner may place the snare shaft and loop within a lumen of the delivery conduit in order to conduct the therapy.

In some instances, the practitioner may desire to change loops during the course of the therapy. For instance, the practitioner may discover, after attempting therapy with the first loop, that a different type of loop would be preferable. In another instance, a first stage of the therapy may be best suited for a first type of loop and the second stage best suited for a second type of loop. In order to change the snare loop, the practitioner may withdraw the shaft from the delivery conduit and couple a second snare loop to the shaft. In some instances, this will be accomplished by first decoupling the first loop and then coupling the second loop to the first end of the shaft. In other instances, the practitioner may couple the second loop to a second end of the shaft, allowing the first loop to remain coupled to the first end of the shaft. If the use of additional loops is desirable, the practitioner could decouple one or more of the first or second loops in order to accommodate further loops. This process may be repeated as necessary to complete the therapy.

FIGS. 3A and 3B are side views of another embodiment of a snare device which can, in certain respects, resemble components of the snare devices described in connection with FIGS. 1, 1A, and 2A-2G above. It will be appreciated that all the illustrated embodiments have analogous features. Accordingly, like features are designated with like reference numerals, with the leading digits incremented to "2." (For instance, the delivery conduit or catheter is designated "100" in FIG. 1 and an analogous delivery conduit or catheter is designated as "200" in FIG. 3A.) Relevant disclosure set forth above regarding similarly identified features thus may not be repeated hereafter. Moreover, specific features of the snare device and related components shown in FIGS. 3A and 3B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the snare device of FIGS. 3A and 3B. Any suitable combination of the features, and variations of the same, described with respect to the snare devices and components illustrated in FIGS. 1A-2G, can be employed with the snare device and components of FIGS. 3A and 3B, and vice versa. This pattern of disclosure applies equally to further embodiments depicted in subsequent figures and described hereafter.

FIGS. 3A and 3B are side views of a snare device in use. The snare device may include a delivery conduit 200 or catheter configured to access an anatomically remote region of the body. The delivery conduit may have a proximal end 202, a distal end 204, and a snare lumen 205 disposed within the conduit between the proximal and distal ends. In the illustrated embodiment, the snare lumen 215 has an opening 210 near the distal end 204 of the delivery conduit 200. The elongate shaft 255 of a snare may be disposed within the snare lumen 205. As illustrated in FIG. 3A, the snare may be deployed through the opening 210 of the snare lumen. A first snare loop 274 is shown coupled to the first end 254 of the elongate shaft 255 by use of an attachment portion 264. The illustrated embodiment also shows the first snare loop 274 being used to surround (in FIG. 3A) and capture (in FIG. 3B) a fragment 50.

The embodiment of FIGS. 3A and 3B also includes a guidewire 217 disposed within the delivery conduit 200 in a guidewire lumen 215. In some instances, a guidewire may be utilized to aid in positioning the delivery conduit within the body of a patient.

FIG. 4A is a side view of another embodiment of a snare device. Like the snare device of FIGS. 3A and 3B, the snare device of FIG. 4A also includes a guidewire 317 disposed within a guidewire lumen 315. The illustrated delivery conduit 300 has two lumens; it will be appreciated that the current disclosure is relevant to devices with a single lumen (as in FIGS. 1 and 1A), two lumens (as in FIGS. 3A-4D), or devices with any number of lumens. FIGS. 4B, 4C, and 4D illustrate exemplary cross sectional profiles of the two lumen delivery conduit 300 of FIG. 4A, taken through lines X-X. These views are exemplary only; it will be appreciated that any cross section known in the art may be utilized. As shown, the delivery conduit 300 may have a circular cross section as in FIGS. 4B and 4D or a "figure 8" as in FIG. 4C. Further, each of the lumens may be circular in cross section, semi-circular, or any other cross sectional shape. For example, in the embodiment of FIG. 4B, both the snare lumen 305 and the guidewire lumen 315 have semi-circular cross sections while both lumens 305, 315 have circular cross sections in the embodiment of FIG. 4C. Moreover, as shown in the embodiment of FIG. 4D, one lumen may be semi-circular while the other is circular. Any combination of these or other cross sectional shapes known in the art is within the scope of this disclosure.

Without further elaboration, it is believed that one skilled in the art can use the preceding description to utilize the present disclosure to its fullest extent. The examples and embodiments disclosed herein are to be construed as merely illustrative and exemplary, and not a limitation of the scope of the present disclosure in any way. It will be apparent to those having skill in the art that changes may be made to the details of the above-described embodiments without departing from the underlying principles of the disclosure herein. It is intended that the scope of the invention be defined by the claims appended hereto and their equivalents.

The invention claimed is:

1. A snare assembly, comprising:
   an elongate shaft having a first end and a second end;
   a first snare loop associated with a first attachment portion configured for coupling the first snare loop to the first end of the shaft;
   a second snare loop associated with a second attachment portion configured for coupling the second snare loop to the second end of the shaft; and
   an elongate outer sheath having proximal and distal ends and a first lumen disposed within the outer sheath between the proximal and distal ends of the outer sheath, the first lumen configured to receive the elongate shaft, the elongate outer sheath further comprising a guidewire lumen configured to facilitate positioning of the elongate outer sheath;
   wherein the first and second snare loops are selectively attachable to the shaft by a medical practitioner.

2. The snare assembly of claim 1, wherein the first snare loop or the second snare loop is coupleable to the shaft by threads.

3. The snare assembly of claim 1, wherein the first snare loop or the second snare loop is coupleable to the shaft by a flute and collet assembly.

4. The snare assembly of claim 1, wherein the first snare loop or the second snare loop is not configured to be decoupled from the shaft once initially coupled.

5. The snare assembly of claim 1, wherein the first snare loop or the second snare loop is configured to be releasably coupled to the shaft.

6. The snare assembly of claim 5, wherein the first snare loop or the second snare loop is configured such that it cannot be decoupled remotely.

7. The snare assembly of claim 1, wherein at least one of the first snare loop or second snare loop comprises a basket loop.

8. The snare assembly of claim 1, wherein the first snare loop circumscribes a larger area than the second snare loop.

9. The snare assembly of claim 1, wherein the first snare loop has a different shape than the second snare loop.

10. The snare assembly of claim 1, wherein the first lumen of the elongate outer sheath further comprises an opening extending through a sidewall of the elongate outer sheath.

11. A snare assembly, comprising:
   an elongate shaft having a first end and a second end;
   a first attachment portion adjacent the first end;
   a second attachment portion adjacent the second end;
   a first snare loop having an attachment portion wherein the first snare loop is configured to be selectively and releasably coupled to either the first attachment portion or second attachment portion;
   a guidewire; and
   an elongate outer sheath having proximal and distal ends and comprising:
      a first lumen disposed within the outer sheath between the proximal and distal ends of the outer sheath, the first lumen configured to receive the elongate shaft, and
      a second lumen disposed within the outer sheath, the second lumen configured to receive the guidewire, wherein the guidewire is configured to facilitate positioning of the elongate outer sheath.

12. The snare assembly of claim 11, further comprising a second snare loop having an attachment portion wherein the second snare loop is configured to be selectively and releasably coupled to either the first attachment portion or second attachment portion.

13. The snare assembly of claim 12, wherein the first lumen of the elongate outer sheath further comprises an opening extending through a sidewall of the elongate outer sheath.

14. A kit comprising:
   a snare assembly comprising,
      an elongate outer sheath comprising an opening extending through a sidewall of the elongate outer sheath;
      an elongate shaft member having a first end and a second end;
      a first attachment portion adjacent the first end and a second attachment portion adjacent the second end wherein the first attachment portion and second attachment portion are configured to be selectively coupled to a snare loop by a medical practitioner; and
      a plurality of snare loops configured to be coupled to the elongate shaft member.

15. The snare assembly of claim 1, wherein the second snare loop is configured for coupling to the first end of the shaft.

\* \* \* \* \*